United States Patent [19]

Stetter et al.

[11] Patent Number: 5,047,352

[45] Date of Patent: Sep. 10, 1991

[54] SELECTIVE CHEMICAL DETECTION BY ENERGY MODULATION OF SENSORS

[75] Inventors: Joseph R. Stetter, Naperville, Ill.; Takaaki Otagawa, Solon, Ohio

[73] Assignee: Arch Development Corporation, Argonne, Ill.

[21] Appl. No.: 300,206

[22] Filed: Jan. 23, 1989

Related U.S. Application Data

[63] Continuation of Ser. No. 736,196, May 20, 1985, abandoned.

[51] Int. Cl.$^5$ .............................................. G01N 1/22
[52] U.S. Cl. .................................... 436/181; 422/98; 436/174
[58] Field of Search ............... 73/23, 27 R, 16, 31.06, 73/23.1, 23.2; 204/424, 408; 338/34; 340/632, 633, 634; 422/90, 94, 98; 436/139, 147, 149, 155, 151

[56] References Cited

U.S. PATENT DOCUMENTS

| | | | |
|---|---|---|---|
| 3,906,473 | 9/1975 | Le Vine | 340/634 |
| 4,384,925 | 3/1983 | Stetter et al. | 204/406 |
| 4,399,684 | 8/1983 | Advani et al. | 73/1 G |
| 4,486,727 | 12/1984 | Fujihira | 204/1 T |
| 4,542,640 | 9/1985 | Clifford | 422/98 X |
| 4,567,475 | 1/1986 | Bukowiecki et al. | 422/98 X |
| 4,670,405 | 6/1987 | Stetter et al. | 436/151 |

FOREIGN PATENT DOCUMENTS 2015154  9/1979  United Kingdom.
2053460  2/1981  United Kingdom.
2140567  1/1984  United Kingdom.

Primary Examiner—David L. Lacey
Assistant Examiner—Thomas E. Daley
Attorney, Agent, or Firm—Larson & Taylor

[57] ABSTRACT

A portable instrument for use in the field in detecting, identifying, and quantifying a component of a sampled fluid includes a sensor which chemically reacts with the component of interest or a derivative thereof, an electrical heating filament for heating the sample before it is applied to the sensor, and modulator for continuously varying the temperature of the filament (and hence the reaction rate) between two values sufficient to produce the chemical reaction. In response to this thermal modulation, the sensor produces a modulated output signal, the modulation of which is a function of the activation energy of the chemical reaction, which activation energy is specific to the particular component of interest and its concentration. Microprocessor which compares the modulated output signal with standard responses for a plurality of components to identify and quantify the particular component of interest. In particular, the concentration of the component of interest is proportional to the amplitude of the modulated output signal, while the identifying activation output energy of the chemical interaction indicative of that component is proportional to a normalized parameter equal to the peak-to-peak amplitude divided by the height of the upper peaks above a base line signal level.

5 Claims, 2 Drawing Sheets

SELECTIVE CHEMICAL DETECTION BY ENERGY MODULATION OF SENSORS

CONTRACTUAL ORIGIN OF THE INVENTION

The U.S. Government has rights in this invention pursuant to Contract No. W-31-109-ENG-38 between the U.S. Department of Energy and The University of Chicago representing Argonne National Laboratory.

This application is a continuation of application Ser. No. 736,196 filed May 20, 1985, now abandoned.

BACKGROUND OF THE INVENTION

The present invention relates to analytic devices and, more particularly to devices for detecting the presence of chemicals in fluids such as air or other gaseous streams. The device has particular application to the identification of unknown components of a fluid sample, such as toxic, hazardous, or other chemicals.

There are many situations where rapid identification of a chemical component of a fluid sample is necessary. For example, in chemical processing it is frequently necessary to monitor a product gas or vapor or effluent from a plant, in medical diagnosis, it is frequently essential to rapidly determine the concentration of gases in specimen samples of blood or exhaled air, in the analytical laboratory, one frequently encounters the need to measure the concentration of one gaseous chemical in the presence of another and this situation is created in the gas chromatographic detector. There are many other instances where it is necessary or desirable to rapidly and selectively determine the concentration of gases.

It is currently possible to analyze substances selectively using expensive and cumbersome analytic equipment. For such purpose it is usually necessary to obtain a sample of the gas and send it to a laboratory for a remote analysis. This is a costly and time consuming process.

Semi-portable versions of more powerful laboratory equipment have been commercially introduced in recent years. But such instruments have certain inherent limitations. Gas chromatographic devices cannot operate in a continuous real-time monitoring mode. Infrared analyzers require a delicate optical system with a rather long absorption path, which contributes to their bulk, weight and unwieldiness. Furthermore, such instruments must usually be operated, and their results interpreted, by well-trained professionals.

Many existing sensors are incapable of detecting chemical components in low concentrations, particularly where the component is substantially non-reactive. In copending application Ser. No. 585,721, filed Mar. 2, 1984, now abandoned, there is disclosed a sensor which catalytically reacts the component of interest to produce a chemically active derivative product which can be readily sensed. But that device, and most semi-portable or field-usable devices are not selective, but are rather specifically designed for detection of a particular chemical component, and are not designed to both detect and identify an unknown component.

Detectors have been developed utilizing an array of electrochemical sensors, each operated in one or more predetermined modes or conditions, the collective responses being analyzed to provide identification of one of a number of gases. Such detectors are disclosed in copending application Ser. No. 585,699, filed Mar. 2, 1984. But such devices are still capable of identifying only a relatively few components, unless a large number of sensors are used, thereby rendering the device more expensive and complicated and less suitable for portable field use.

Virtually all prior detection devices utilize a sensor which produces a steady-state output signal which changes when the chemical/physical environment changes. The design goal of such devices is generally to eliminate sensitivity to all but one environmental parameter or chemical, thus producing a useful monitoring and measurement tool for that parameter or chemical. But the practical achievement of this goal is extremely difficult. For example, pressure transducers may be susceptible to temperature variations and methane sensors tend to respond to most hydrocarbons. Expensive measures must frequently be taken to minimize this cross sensitivity.

Typical chemical sensors are defined as devices that change an output characteristic (e.g., current, voltage, absorbence, resistance, fluorescence, size, etc.) when exposed to the chemical of interest. The change in response is usually examined at equilibrium or steady-state and the magnitude of the response is related to the concentration. Great care is taken to make sure that the device is designed so that the response only occurs when the chemical of interest is present. This steady-state approach does not provide sufficient data to resolve hundreds or perhaps thousands of chemicals that may be present in a sample using a single sensor, instrument, or sensor array.

U.S. Pat. No. 4,399,684 discloses a gas measuring method wherein a metal-oxide gas sensor is sequentially heated and cooled during exposure to a sample gas. The patent discloses that during such thermal cycling a continuous, concentration-dependent, unique signature for different gas concentrations is produced. This signature comprises a ratio of two samples of the sensor output signal taken at predetermined times during the thermal cycle. This signature yields sufficient information to identify the gas concentration by comparison to standard signatures for known concentrations. But because the signatures developed are concentration-dependent, they cannot be used to identify an unknown component of the sample. The patent implies that the method disclosed may be used to identify an unknown gas, but it gives no explanation of how such an identification could be effected.

SUMMARY OF THE INVENTION

It is general object of the present invention to provide an improved detection device and method which avoids the disadvantages of prior devices and methods, while affording additional structural and operating advantages.

An important object of the invention is the provision of a method of identifying an unknown component of a fluid sample, which method is uniquely suitable for field application.

In connection with the foregoing object, another object of the invention is the provision of a method of determining the concentration of the identified chemical.

Another object of the invention is the provision of a method of the type set forth which is capable of identifying a large number of chemical components by the use of a single sensing means.

In connection with the foregoing objects, it is another object of the invention to provide a method of the type set forth which utilizes a sensor in a dynamic mode to determine a dynamic or chemical reaction-related parameter.

Another object of the invention is the provision of a detection device which incorporates the method of the foregoing objects.

Yet another object of the invention is the provision of such a detection device which operates by energy modulation of the sensing means.

Another object of the invention is the provision of a sensing device of the type set forth, which is of simple and ecomonical construction and characterized by small, compact size.

Still another object of the invention is the provision of a detection method and apparatus of the type set forth which affords rapid and selective determination of the identity and concentration of chemical components.

It is another object of the invention to provide a detection method and device of the type set forth, which permits detection of very low concentration levels of chemical components.

These and other objects of the invention are attained by providing a method for identifying a component of a fluid sample, comprising the steps of: exposing the fluid sample to a sensing unit have an energy input and adapted for interaction with the component to produce a response, the interaction having a parameter which varies with the interacting component, modulating the energy input to produce a modulated response proportional to the parameter, and measuring the parameter from the modulation of the response characteristic for identifying the component. In other words, the incoming chemical is reacted, the extent of the reaction being modulated in a cyclical or otherwise regular pattern and this extent of reaction is followed by the sensing means. The information produced in this modulated record is sufficient to provide the identity and concentration of the chemical entering this sensing means.

Additioinal objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DESCRIPTION OF THE FIGURES

For the puspose of facilitating an understanding of the invention, there is illustrated in the accompanying drawings a preferred embodiment thereof, from an inspection of which, when considered in connectin with the following description, the invention, its construction and operation, and many of its advantages should be readily understood and appreciated.

DESCRIPTION OF THE PREFERRED EMBODIMENT

In its broadest aspect, the present invention involves the generation of a large amount of information or data about a sample medium with the use of a single sensing apparatus by the technique of modulating the sensor signals. More particularly, the invention resides in energy modulation of an interactin between the sensor and the components to be detected, thereby producing a modulated output signal from the detector, and using this modulation information to derive a parameter (related to the kinetic or thermodynamic characteristics of a chemical or chemical reaction) which parameter can be used to determine the identification and concentration of the component of interest. While it is possible to use a number of different types of sensors and modulation means for ascertaining different parameters specific to a chemical of interest, the preferred embodiment described below utilizes thermal modulation of an electrochemical sensor signal for determining a kinetic parameter representative of the "activation energy" of a chemical reaction with air for the chemical being detected, identified, and quantified by the sensor system (modulator and sensor).

Figure 1:
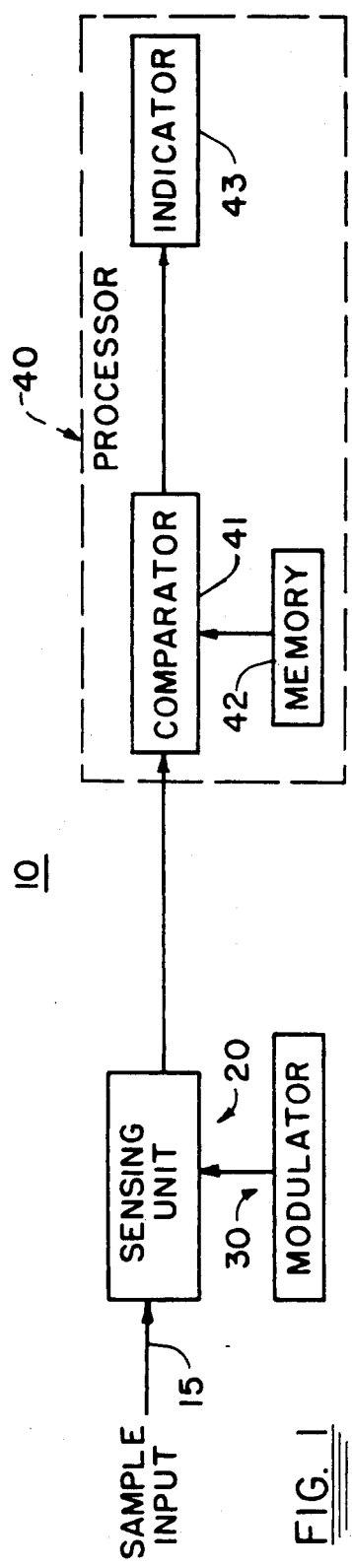
FIG. 1 is a block diagram of a detection apparatus constructed in accordance with and embodying the features of the present invention.
Figure 2:
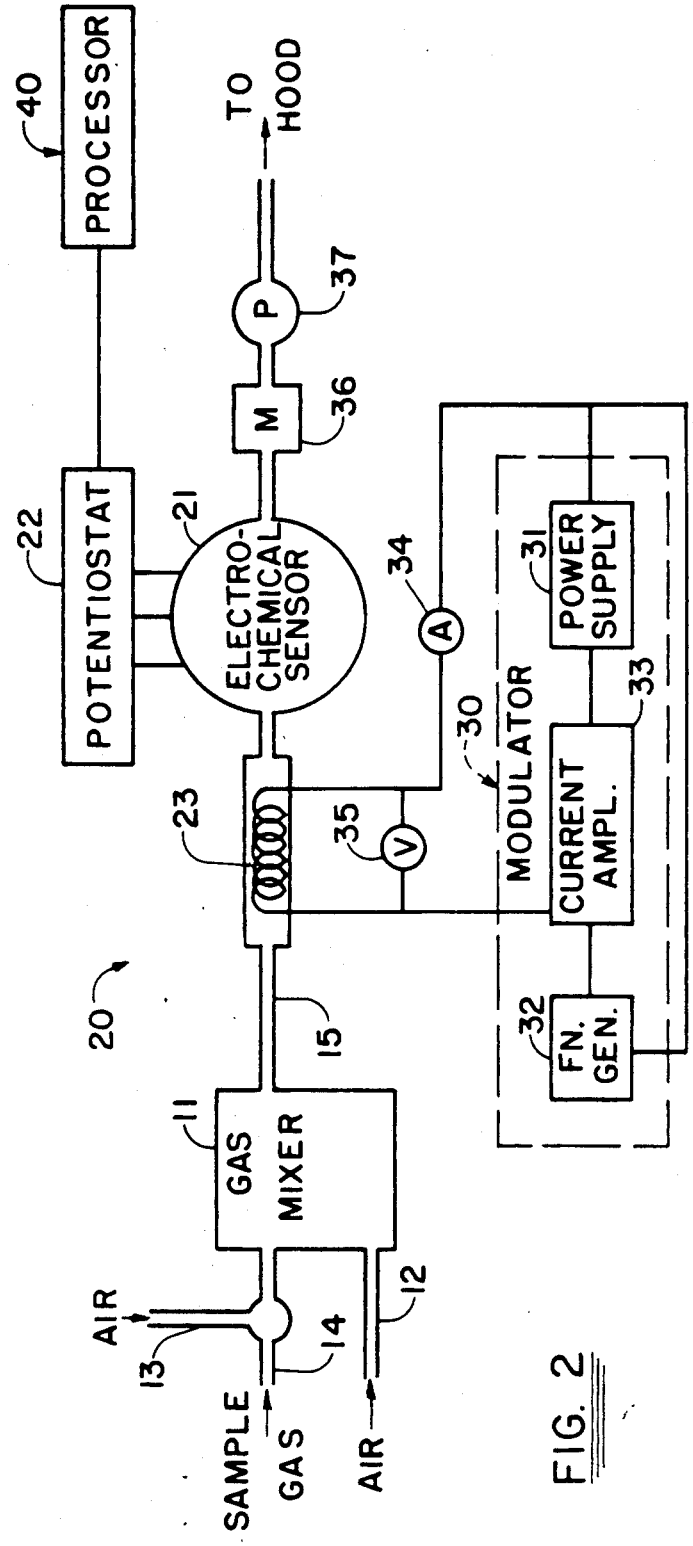
FIG. 2 is a further block diagram of the sensing apparatus, showing a particular type of sensing unit and modulator in greater detail.

Referring to FIGS. 1 and 2, there is illustrated a detector, generally designated by the numeral 10, constructed in accordance with and embodying the features of the present invention. The detector 10 includes a gas mixer 11, an air inlet 12 and another inlet which is coupled through a suitable valve to either an air inlet 13 or a sample gas inlet 14. By this arrangement, either ambient air containing chemical components to be detected can be emitted directly to the gas mixer 11, or laboratory samples to be identified can be mixed in the gas mixer 11 with air to a desired concentration range prior to analysis by the modulator/sensor. It will be appreciated that the gas mixer 11 is optional and that if desired ambient air or other source of a sample to be detected could be coupled directly to the remainder of the detector 10.

The gas mixer 11 has an outlet 15 which is coupled to the inlet of a sensing unit 20. More particularly, the sensing unit 20 includes an electrochemical sensor 21 coupled to a potentiostat 22 for regulating electrode potentials and performing electro-oxidation of electro-reduction of the chemicals that enter the sensor. The sensing unit 20 also includes a heating filament 23 for heating the gas sample before it is admitted to the electrochemical sensor 21. The filament 23 serves not only as a heater, but preferably also acts as a catalytic or chemical reactor. The filament 23 may be of a suitable material, e.g. noble metals like Pt, Pd, Rh, Au, Ir, or other catalyst, depending upon the types of chemical components to be detected, and the particular electrochemical sensor 21 being used. In an experimental model of the invention, the filament 23 is formed of a noble metal, such as Rh, but it will be appreciated that non-noble metal catalysts such as tungsten or molybdenum could also be used. Further, any "microcatalytic"

reactor capable of producing repeatable and rapid (e.g. more rapid than sensor response) modulation can be used.

The filament 23 is coupled to the modulator 30 which includes a power supply 31, a function generator 32 and a current amplifier 33. More particularly, the power supply 31 is coupled to both the function generator 32 and the current amplifier 33. The function generator 32 produces an output signal of predetermined waveform, such as a sawtooth wave, which is applied through the current amplifier 33 to one terminal of the filament 23. The other terminal of the filament 23 is connected through an ammeter 34 to the power supply 31. A voltmeter 35 may be connected across the terminals of the filament 23. It will be appreciated that the current through the filament 23 and therefore the temperature thereof, is modulated by the output signal from the function generator 32, as will be explained more fully below.

The sample gas exits the electrochemical sensor 21 and passes through a flow meter 36 and a pump 37 to a suitable venting hood (not shown) or the like. This provides safe discharge of any chemicals that may be toxic or hazardous.

The electrochemical sensor 21 produces an electrical output signal which is produced by the potentiostat 22 and read by an electronic processor 40, which may include a microprocessor circuit. Preferably, the processor 40 includes a comparator 41 which receives the output signal from the sensing unit 20, and which is also coupled to a suitable memory 42, such as a semiconductor memory. Standard response parameters for a plurality of different chemical components are stored in the memory 42. The modulation of the filament 23 causes a corresponding modulation of the output signal from the electrochemical sensor 21 to produce a characteristic output response parameter. This response parameter is compared in the comparator 41 with the standard response parameters stored in the memory 42, and if a match is detected a suitable indication of the identity and concentration of the detected chemical component is produced in an indicator 43, which may be of any desired type. For example, the indicator 43 may produce a readout on a digital display, such as a CRT or other type of display.

Figure 3A:
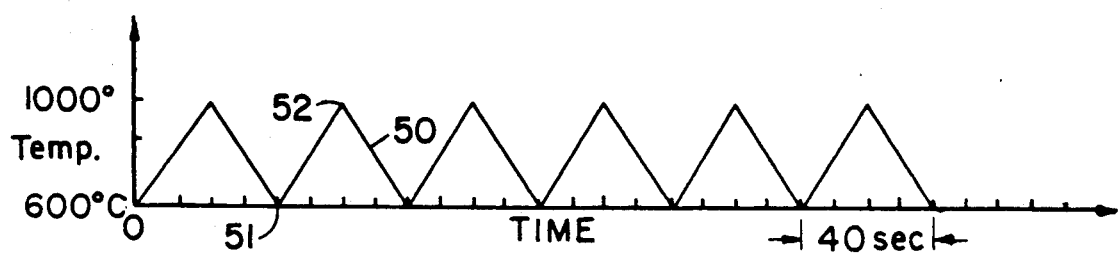
FIG. 3A is a graph of the modulation of the heating element temperature.
Figure 3B:
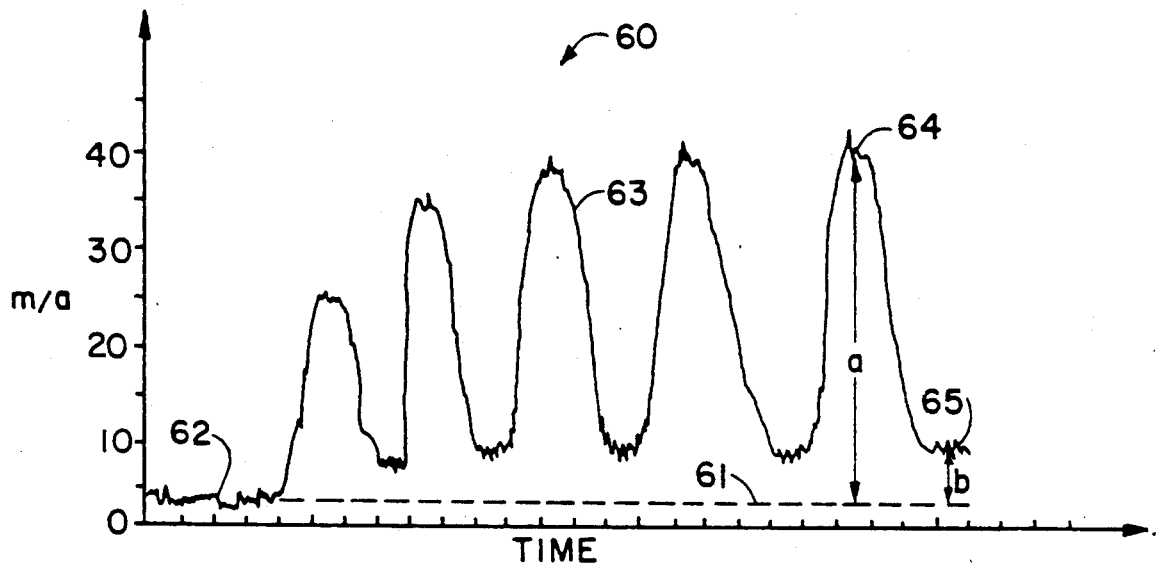
FIG. 3B is a graph of the modulated output from the sensing unit, on the same time base as FIG. 3A when the input gas is 200 ppm cyclohexane in air.

Referring now also to FIGS. 3A and 3B, the operation of the detector 10 will be explained by way of example, in connection with the detection of cyclohexane. For this purpose, the electrochemical sensor 21 is a CO sensor, and the filament 23 is a Rh filament. Air contaminated with 200 ppm cyclohexane is passed over the filament 23 and thence to the sensor 21. Preferably, the modulator 30 is capable of varying temperature of the filament 23 between ambient and about 1500° C., but the actual range of variation will be determined by the output signal from the function generator 32.

The filament 23 produces a pyrolysis reaction of cyclohexane in accordance with the reaction cyclohexane + air (20% oxygen) = CO + products. At low temperatures, e.g., less than about 200° C., little or no pyrolysis of cyclohexane occurs, i.e., the reaction rate is very low at this temperature and, therefore, the electrochemical sensor 21 reads zero. But as the temperature is raised, this reaction begins to proceed at an appreciable rate, and the sensor 21 responds to the increase in CO concentration.

The usual kinetic expression for the rate of CO production is $$d[CO]/dt = r[\text{cyclohexane}][\text{air}][C]$$

where [C] is the concentration of catalyst, usually taken to the first power, and r is the rate constant. The concentration of air or cyclohexane can be taken to any power. The rate constant can be written $$r = Ae^{-E/kT}$$

where A is a pre-exponential factor, T is the absolute temperature, k is Boltzmann's constant, and E is the activation energy for the reaction.

In this case, the function generator 32 produces a sawtooth output waveform, which results in a sawtooth modulation of the filament temperature in accordance with the waveform 50 in FIG. 3A, the temperature undergoing one complete cycle in about 40 seconds. The temperature cycles between a low point 51 of about 600° C. and a high point 52 of about 1000° C. This modulation of the filament temperature continuously varies the rate of CO production to produce a modulated output signal from the sensor 21, indicated by the waveform 60 in FIG. 3B. Line 61 in FIG. 3B designates the background or base line level, i.e., the output produced by the sensor 21 in response to pure air, the actual pure air response signal being indicated by a portion 62 of the waveform. As the gas sample bearing the cyclohexane contaminant is admitted to the sensor 21 its response builds up and approaches a steady state level indicated by the right-hand portion of the waveform 60. As can be seen, this response is a modulated signal 63 which varies between upper peaks 64 and lower peaks 65. The peak-to-peak amplitude of the signal 63 is a−b, where a is the distance between the base line 61 and the upper peak 64, and b is the distance between the base line 61 and the lower peak 65.

It can be seen from the kinetic expression for the rate of CO production, above, that the rate of CO production and, therefore, the sensor output signal, will be proportional to the cyclohexane concentration if the concentration of air and catalyst are held virtually constant. Also, it can be seen that a concentration-independent parameter is the rate of CO production divided by the cyclohexane concentration, which is $$d[CO]/[\text{cyclohexane}]dt = r[\text{air}][C]$$

and is a constant at constant concentration and temperature. Thus, from the aforementioned expression for the rate constant r, it can be seen that the temperature change in the filament produces a changing CO concentration that is determined by the pre-exponential factor A and the activation energy E. This reaction rate constant r is very specific for chemical reactions. Thus, the thermally modulated CO concentration divided by the cyclohexane concentration is proportional to the activation energy characteristic for the production of CO from cyclohexane over a heated Rh filament. Because the CO concentration divided by the cyclohexane concentration is independent of the cyclohexane concentration, this information can be used to identify the contaminant as cyclohexane.

Figure 4:
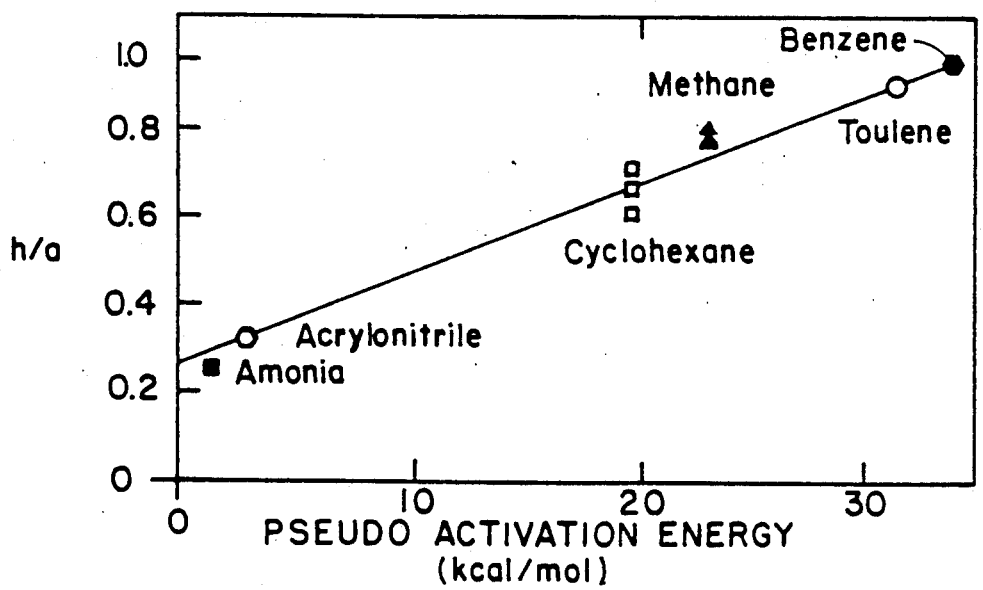
FIG. 4 is a graph of the parameter h/a vs. pseudo-activation energy for formation of electrochemically active compounds on a Rh filament, illustrating the characteristic pesudo-activation energy for a number of different chemicals.

This information is expressed by the normalized parameter h/a, where h=a−b, i.e., the peak-to-peak amplitude of the waveform 60 divided by the magnitude or height of the upper peaks 64. The magnitude of the height of the upper peaks 64 is found to be proportional to the cyclohexane concentration. It has also been found that the parameter h/a is proportional to a pseudo-activation energy in kcal/mol for a number of chemical components studied, including ammonia, acrylonitrile, cyclohexane, methane, toluene and benzene, as illustrated in FIG. 4. It has also been found that the peak-to-peak amplitude h of the signal response waveform 60, as well as the height "a" of the upper peaks 64, is proportional to the concentration of the chemical component being detected.

Thus, the processor 40 operates on the output waveform 60 from the sensing unit 20 to determine the quantity h and the parameter h/a, and compares this parameter with standard parameters (i.e. the pseudo-activation energies) stored in the memory 42 to identify the contaminant as cyclohexane and to register the concentration thereof.

In the preferred embodiment just described, the catalytic surface of the filament 23 is separate from the electrochemical sensor 21. But it will be appreciated that the principles of the present invention could also be utilized in a reaction scheme wherein the temperature of a semiconductor sensor is modulated to produce a catalytic reaction, and then the same surface is used as the gas detector.

While, in the preferred embodiment, thermal modulation of an electrochemical CO sensor has been described for detecting hydrocarbons, it will be appreciated that the principles of the present invention apply to other types of sensors and other types of modulation of other types of interactions. Thus, for example, benzene could be detected by modulating the photon energy input to a photoionization detector for measuring the ionization potential of the interaction. Infrared radiation input to a thermopile detector could be modulated to measure the infrared absorption coefficient for detecting chemicals which are strong infrared absorbers, such as methane. Similarly, thermal energy input to a thermionic ionization detector could be modulated to measure ionization potential. Another alternative would be the modulation of a chemical reagent, e.g., ozone, in a chemi-luminescence detector for measuring related kinetic parameters, e.g., rate order. Such a technique might be useful in detecting nitric oxide, for example. Another technique could involve the use of magnetic field modulation with a microwave detector for measuring magnetic energy levels of electrons with unpaired spins, which technique could be used for detecting odd molecules with unpaired electrons. In general, all that is necessary is to provide a means (e.g. energy input) to chemically or otherwise modulate the interaction of the chemical to be detected in the sample and then a means to detect the modulated signal. Then one is able to determine the specific kinetic or thermodynamic parameters that describe the situation and this provides the selective information desired to identify and quantify the chemical of interest.

A significant aspect of the invention is that it provides selective identification of a large number of chemical components utilizing a detector with a minimal number of parts, resulting in a detector with wide application which can be conveniently miniaturized for portability and field use. Furthermore, it will be appreciated that the detector of the present invention can be designed to produce unambigous output indications so that it can be used by non-skilled personnel.

While the present invention has been described in terms of operation with gaseous samples, it will be appreciated that the principles of the invention could also be applied to analysis of chemicals in a liquid medium.

The embodiments of the invention in which an exclusive property or privilege is claimed are defined as follows:

1. A method for identifying an unknown component of a gas sample comprising the steps of passing the gas sample through a single sensing unit containing a separate modulator component and a filament operatively connected to the modulator component, modulating the temperature of the filament to produce a modulated reactive response in the unknown component of the gas sample, passing the modulated reacted gas sample into a separate electrochemical cell to produce a modulated sensor signal of the unknown component in the gas sample, converting the modulated sensor signal of the unknown component to a concentration independent value, comparing the concentration independent value of the modulated sensor signal of the unknown component with those of known responses for various components previously stored within the memory of a computer to determine the presence or absence of the unknown components having known responses previously stored.

2. The method of claim 1 wherein the temperature is constantly varied between two temperatures sufficient to produce an interaction with the unknown component.

3. The method of claim 2 wherein the temperature is varied between 600° C. and 1000° C.

4. An instrument for identifying an unknown component of a gas sample, said instrument comprising an inlet for receiving the gas sample, a single cell in communication with said inlet, said single cell having a filament therein, a separate modulator operatively connected to the filament in said single cell for continuously modulating the temperature of the filament to produce a modulated reactive response in the unknown component of the gas sample, an electrochemical sensor means in communication with said single cell, for sensing the modulated reactive response in the unknown component of the gas sample and providing an oscillating waveform response thereto, means for processing the oscillating waveform response to convert the modulated response to concentration independent values, memory means for storing concentration independent values of modulated responses of various known gas components, and means for comparing the concentration independent values of the modulated response in the unknown component of the gas sample with the concentration independent values stored in said memory means to determine the presence or absence of the known gas components having concentration independent values stored in said memory means so that in the event the concentration independent value of the modulated response of the unknown component matches the concentration independent value of one of the known gas components the unknown component is identified.

5. The instrument of claim 4 wherein said filament is a metal selected from the group consisting of Pt, Rh, Ir, Au, or Pd or an alloy thereof disposed for exposure to the gas sample.

* * * * *